United States Patent
Lim et al.

(10) Patent No.: US 11,590,048 B2
(45) Date of Patent: Feb. 28, 2023

(54) METHOD AND DEVICE FOR CONTROLLING WALKING ASSIST DEVICE

(71) Applicant: Samsung Electronics Co., Ltd., Suwon-si (KR)

(72) Inventors: Bokman Lim, Yongin-si (KR); Kyung-Rock Kim, Yongin-si (KR); Jusuk Lee, Suwon-si (KR); Jun-Won Jang, Seoul (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 214 days.

(21) Appl. No.: 16/520,769

(22) Filed: Jul. 24, 2019

(65) Prior Publication Data
US 2020/0214925 A1 Jul. 9, 2020

(30) Foreign Application Priority Data
Jan. 4, 2019 (KR) .......... 10-2019-0001189

(51) Int. Cl.
*A61H 3/00* (2006.01)
*G16H 50/20* (2018.01)

(52) U.S. Cl.
CPC .......... *A61H 3/00* (2013.01); *G16H 50/20* (2018.01); *A61H 2003/007* (2013.01); *A61H 2201/164* (2013.01); *A61H 2201/165* (2013.01); *A61H 2201/1628* (2013.01); *A61H 2201/5007* (2013.01); *A61H 2201/5058* (2013.01);
(Continued)

(58) Field of Classification Search
None
See application file for complete search history.

(56) References Cited

U.S. PATENT DOCUMENTS

| | | | |
|---|---|---|---|
| 2010/0049102 A1 | 2/2010 | Yasuhara | |
| 2015/0099253 A1* | 4/2015 | De Roy | A61F 2/64 434/274 |

(Continued)

FOREIGN PATENT DOCUMENTS

| | | |
|---|---|---|
| CN | 106176149 A | 12/2016 |
| JP | 2015-164451 A | 9/2015 |

(Continued)

OTHER PUBLICATIONS

Zhang, Juanjuan et al. "Human-in-the-loop optimization of exoskeleton assistance during walking" Science.org. Jun. 23, 2017. (Year: 2017).*

(Continued)

*Primary Examiner* — Samchuan C Yao
*Assistant Examiner* — Savannah L Gabriel
(74) *Attorney, Agent, or Firm* — Harness, Dickey & Pierce, P.L.C.

(57) ABSTRACT

A method and device for controlling a walking assist device is disclosed. The method includes determining a first state variable for a gait state of a user wearing the walking assist device based on a gait of the user, obtaining a second state variable which is smoothed and time-delayed from the first state variable, obtaining a third state variable by applying a torque control variable to the second state variable, and determining an assist torque to be provided by the walking assist device based on the obtained third state variable.

19 Claims, 16 Drawing Sheets

(52) U.S. Cl.
CPC ............... *A61H 2201/5061* (2013.01); *A61H 2201/5069* (2013.01)

(56) References Cited

U.S. PATENT DOCUMENTS

| | | | |
|---|---|---|---|
| 2015/0190923 A1* | 7/2015 | Seo | A61H 1/0266 602/16 |
| 2016/0030201 A1* | 2/2016 | Zoss | A61H 3/00 623/24 |
| 2016/0074180 A1* | 3/2016 | Lenzi | A61F 2/6607 623/24 |
| 2016/0074272 A1* | 3/2016 | Ahn | A61B 5/112 623/24 |
| 2016/0338897 A1* | 11/2016 | Takenaka | A61H 3/00 |
| 2017/0340506 A1* | 11/2017 | Zhang | A61H 3/00 |
| 2018/0193172 A1* | 7/2018 | Smith | A61F 2/70 |
| 2018/0272525 A1* | 9/2018 | Kumeno | B25J 9/1638 |
| 2018/0360347 A1 | 12/2018 | Lim et al. | |
| 2019/0160321 A1* | 5/2019 | Ozsecen | A63B 24/0062 |
| 2019/0240103 A1* | 8/2019 | Hepler | A61H 3/00 |
| 2020/0331150 A1* | 10/2020 | Vitiello | B25J 13/088 |
| 2021/0022944 A1* | 1/2021 | Barnes | A61H 3/00 |

FOREIGN PATENT DOCUMENTS

| | | |
|---|---|---|
| KR | 1323019 | 10/2013 |
| KR | 20180136656 A | 12/2018 |
| KR | 20190032925 A | 3/2019 |
| WO | WO-2012/100250 A1 | 7/2012 |

OTHER PUBLICATIONS

Wu, Qingcong et al. "Design and control of powered hip exoskeleton for walking assistance," International Journal of Advanced Robotic Systems. Mar. 13, 2014. (Year: 2014).*

C. Abdallah et al., "Delayed Positive Feedback Can Stabilize Oscillatory Systems", Mar. 21, 2003.

Juanjuan Zhang, et al., "Human-in-the-loop optimization of exoskeleton assistance during walking", Science 356, pp. 1280-1284, Jun. 23, 2017.

Jun Morimoto et al., "Poincare-Map-Based Reinforcement Learning for Biped Walking", Proceedings of the 2005 IEEE, International Conference on Robotics and Automation, Barcelona, Spain, Apr. 2005.

Ye Ding et al., "Human-in-the-loop optimization of hip assistance with a soft exosuit during walking", Science Robotics, Research Article, Sci, Robot. 3, eaar5438, Feb. 28, 2018.

Rui Huang et al., "Interactive Learning for Sensitivity Factors of a Human-Powered Augmentation Lower Exoskeleton", 2015 IEEE/RSJ International Conference on Intelligent Robots and Systems (IROS), Congress Center Hamburg, Germany, Sep. 28-Oct. 2, 2015.

Rui Huang et al., "Hierarchical Interactive Learning for a Human-Powered Augmentation Lower Exoskeleton", 2016 IEEE International Conference on Robotics and Automation (ICRA), Stockholm, Sweden, May 16-21, 2016.

Wenxia Xu et al., "Study of Reinforcement Learning Based Shared Control of Walking-aid Robot", Proceedings of the 2013 IEEE/SICE International Symposium on System integration, Kobe International Conference Center, Kobe, Japan, Dec. 15-17, 2013.

Masashi Hamaya et al., "Learning Task-Parametrized Assistive Strategies for Exoskeleton Robots by Multi-Task Reinforcement Learning", 2017 IEEE International Conference on Robotics and Automation (ICRA), Singapore, May 29-Jun. 3, 2017.

Extended European Search Report dated Mar. 9, 2020 for corresponding EP Application No. 19194962.7.

* cited by examiner

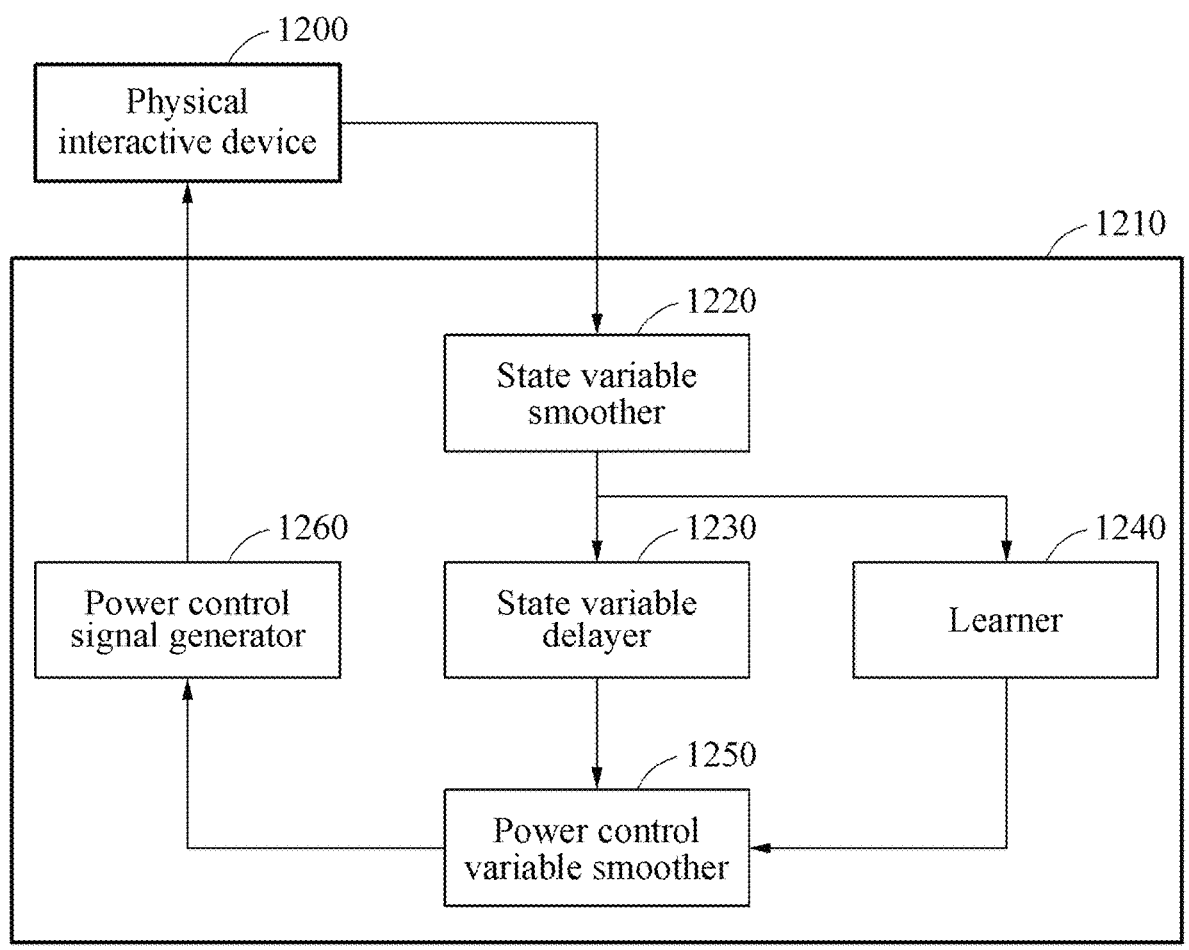

METHOD AND DEVICE FOR CONTROLLING WALKING ASSIST DEVICE

CROSS-REFERENCE TO RELATED APPLICATION

This application claims under 35 U.S.C. § 119 to Korean Patent Application No. 10-2019-0001189 filed on Jan. 4, 2019, in the Korean Intellectual Property Office, the entire contents of which are incorporated herein by reference in their entirety.

BACKGROUND

1. Field

At least one example embodiment relates to a walking assist device and/or a method of controlling the walking assist device.

2. Description of the Related Art

A walking assist device may be used to assist a user who experiences inconvenience in walking more readily. Such an inconvenience in walking may be attributed to various reasons, for example, diseases or accidents, and the user cannot walk readily on her/his own due to such reasons. In such a case, the walking assist device may be used to assist the user during a walking exercise as a part of a rehabilitation. In addition, a recent issue of aging societies has contributed to a growing number of people who experience inconvenience and pain from reduced muscular strength or joint problems due to aging. Thus, there is a growing interest in walking assist devices that enable elderly users or patients with reduced muscular strength or joint problems to walk with less effort.

A walking assist device may be worn on a body of a user to provide the user with power needed to walk, and assist the user with walking in a normal gait pattern. The walking assist device may interact directly with the body of the user, and thus a high level of safety may be needed.

SUMMARY

At least one example embodiment relates to a method of controlling a walking assist device configured to be worn by a user.

In at least one example embodiment, the method may include determining a first state variable for a gait phase of the user based on a gait of the user; obtaining a second state variable by smoothing and time-delaying the first state variable; obtaining a third state variable by applying a torque control variable to the second state variable; and determining an assist torque provided by the walking assist device based on the third state variable.

In some example embodiments, the method may include determining the torque control variable in response to the gait phase in a gait cycle of the user corresponding to a set gait phase.

In some example embodiments, the method may include smoothing the torque control variable to generate a smoothed torque control variable, wherein the obtaining of the third state variable includes obtaining the third state variable by applying the smoothed torque control variable to the second state variable.

In some example embodiments, in a normal mode, the determining of the torque control variable includes determining a desired torque control variable by applying a state variable value corresponding to a current gait phase in the gait cycle of the user to a torque control variable determining function based on parameters derived from a previous learning result.

In some example embodiments, in a learning mode, the determining of the torque control variable includes determining a retrieval torque control variable generated based on a probability function, and setting the retrieval torque control variable as the torque control variable.

In some example embodiments, in the learning mode, the determining of the torque control variable further includes determining a score of a previous torque control variable based on a walking assist power index determined from a previous gait of the user; and determining whether the score satisfies a condition.

In some example embodiments, the walking assist power index includes, a first walking assist power index indicating a magnitude of walking assist power transferred by the walking assist device, and a second walking assist power index indicating a degree of hindrance to the user in walking by the walking assist device.

In some example embodiments, the determining of the score includes determining the score based on a weighted sum of the first walking assist power index and the second walking assist power index.

In some example embodiments, the determining of the first state variable includes determining the first state variable based on hip joint angle information of the user measured by a sensor of the walking assist device.

In some example embodiments, the obtaining of the second state variable includes smoothing the first state variable to generate a smoothed first state variable; and obtaining the second state variable by time-delaying the smoothed first state variable.

In some example embodiments, the smoothing includes obtaining the smoothed first state variable based on the first state variable determined for a current gait cycle and the first state variable determined for a previous gait cycle.

Some example embodiments relate to a non-transitory computer-readable medium comprising computer readable instructions that, when executed by a computer, cause the computer to perform the method of controlling the walking assist device.

At least one example embodiment relates to a device configured to control a walking assist device.

In at least one example embodiment, the device may include a memory; and a controller configured to control an assist torque provided by the walking assist device based on a gait of a user wearing the walking assist device by, determining a first state variable for a gait phase of the user based on the gait, obtaining a second state variable by smoothing and time-delaying the first state variable, obtaining a third state variable by applying a torque control variable to the second state variable, and determining the assist torque to be provided by the walking assist device based on the third state variable.

In some example embodiments, the controller is configured to, determine the gait phase in a gait cycle of the user based on the first state variable, and determine the torque control variable in response to the gait phase corresponding to a set gait phase.

In some example embodiments, the controller is configured to, obtain the third state variable by, smoothing the torque control variable to generate a smoothed torque control variable, and applying the smoothed torque control variable to the second state variable.

In some example embodiments, the controller is configured to operate in a learning mode to, determine the torque control variable, determine a score of a previous torque control variable based on a walking assist power index determined from a previous gait of the user, determine a retrieval torque control variable generated based on a probability function, in response to the score not satisfying a set condition, and set the retrieval torque control variable as the torque control variable.

In some example embodiments, the walking assist power index includes, a first walking assist power index indicating a magnitude of walking assist power to be transferred by the walking assist device, and a second walking assist power index indicating a degree of hindrance to the user in walking by the walking assist device.

At least one example embodiment relates to a walking assist device.

In at least one example embodiment, the walking assist device may include a sensor configured to measure a gait of a user wearing the walking assist device; a driver configured to operate an actuator of the walking assist device to provide an assist torque to the user based on a torque control signal; and a controller configured to generate the torque control signal to control the assist torque based on the gait measured by the sensor by, determining a first state variable for a gait phase of the user based on the gait, obtaining a second state variable by smoothing and time-delaying the first state variable, obtaining a third state variable by applying a torque control variable to the second state variable, and determining the assist torque provided by the walking assist device based on the third state variable.

In some example embodiments, the controller is configured to, determine the gait phase in a gait cycle of the user based on the first state variable, and determine the torque control variable in response to the gait phase corresponding to a set gait phase.

In some example embodiments, the controller is configured to, obtain the third state variable by, smoothing the torque control variable to generate a smoothed torque control variable, and applying the smoothed torque control variable to the second state variable.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 12 is a diagram illustrating a configuration of a system for controlling a physical interactive device according to at least one example embodiment.

DETAILED DESCRIPTION

Figure 1:
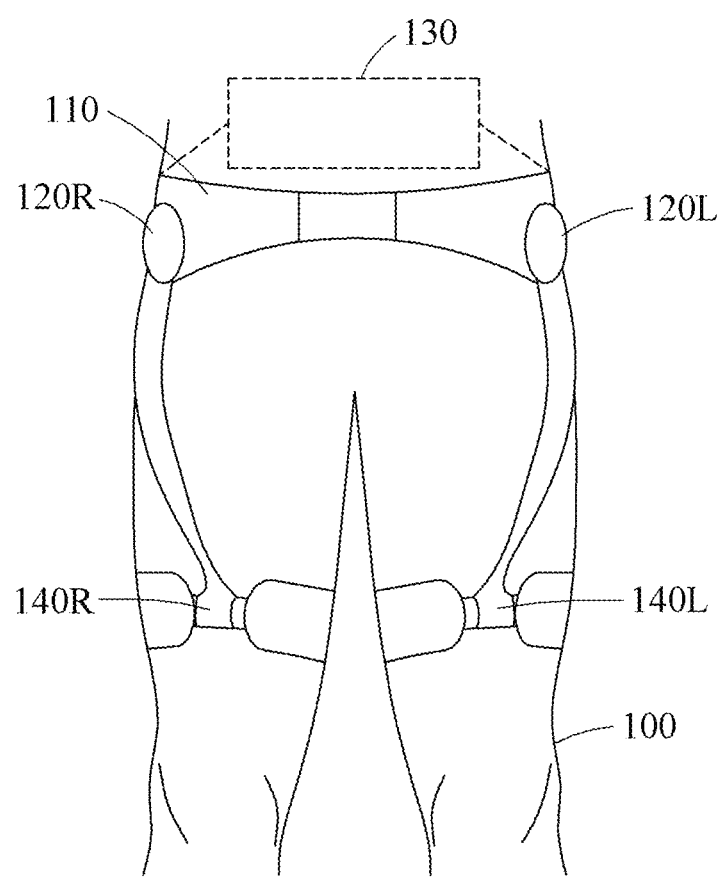
FIG. 1 is a diagram illustrating a walking assist device worn on a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

Hereinafter, examples will be described in detail with reference to the accompanying drawings, and like reference numerals in the drawings refer to like elements throughout.

FIG. 1 is a diagram illustrating a walking assist device worn on a user according to at least one example embodiment.

A walking assist device 110, or a gait assist device, may assist a user 100 wearing the walking assist device 110 in walking readily. The walking assist device 110 may assist or support a portion of a leg or an entire leg of the user 100 to help the user 100 walk more readily. The walking assist device 110 may be provided in a wearable exoskeleton type as illustrated in FIG. 1, and configured to assist or support muscular strength of the user 100 when the user 100 walks to improve a walking movement or a gait of the user 100 or enable the user 100 to walk normally. For example, when a general user or an elderly user with reduced muscular strength wears the walking assist device 110, the walking assist device 110 may increase a walking ability of the user by enabling the user to walk for a longer period of time as compared to when the user does not wear the walking assist device 110, and enable the user to walk independently by providing or adding power needed for the user to walk. The walking assist device 110 may also be used in such fields as rehabilitation and walking correction by improving abnormal walking of a patient. The type of the walking assist device 110 illustrated in FIG. 1 is provided as an example, and example embodiments described herein may thus be applicable to other types of walking assist devices.

Referring to FIG. 1, the walking assist device 110 generates a torque, or a rotational force, at left and right hip joints 120L and 120R under the control of a controller 130, and the generated torque provides legs of the user 100 with power for flexion and extension through transferrers 140L and 140R disposed above knees of the user 100. The walking assist device 110 measures a walking movement, or a gait, of the user 100 through a sensor thereof, and estimates a gait state or a gait phase in a gait cycle of the user 100 based on the measured gait. The walking assist device 110 determines a direction in which power is to be provided to each of the legs and an amount of the power to be provided, at a current point in time, based on the estimated gait phase.

The walking assist device 110 is worn on a body of the user 100 such that the walking assist device 110 applies power to the user 100 while receiving power applied by the user 100. Thus, there is an interaction between the user 100 and the walking assist device 110. In such interaction, a reaction to a physical intervention of the walking assist device 110 may vary from individual to individual. That is, individuals may react differently to a same physical intervention.

Thus, one or more example embodiments, may individualize the walking assist device 110 by determining a rule for adjusting a control variable of the walking assist device 110 to be suitable for each individual user. The foregoing term "individualization" indicates that a control policy or rule of the walking assist device 110 may be applied differently to individual users based on a difference in individual gait characteristic, physical state, muscular strength, and the like. The individualization may be achieved by learning the control policy of the walking assist device 110 based on a measured gait state of a user.

The example embodiments to be described hereinafter provide a safe and consistent walking assistance performance through the individualization of the walking assist device 110 based on a state variable and a torque control variable to which a walking movement, or a gait, of a user is applied. For the safe and consistent walking assistance performance, a smoother and/or a delayer may be used, and reinforcement learning that improves (or, alternatively, optimizes) parameters for the control policy may be performed. Through the reinforcement learning, it is possible to improve assistance transfer power by increasing a rate indicating how much an assist torque provided to the user 100 by the walking assist device 110 is to be useful for the user 100 in walking, and to reduce a mismatch in walking assistance by decreasing a rate indicating how much assist power provided to the user 100 by the walking assist device 110 hinders the user 100 in walking. In addition, it is possible to provide a walking assistance customized (or, alternatively, optimized) for an individual user, reduce an amount of energy needed for walking, and improve levels of walking regularity, walking safety, and walking stability. Hereinafter, the example embodiments will be described in detail with reference to the accompanying drawings.

Figure 2:
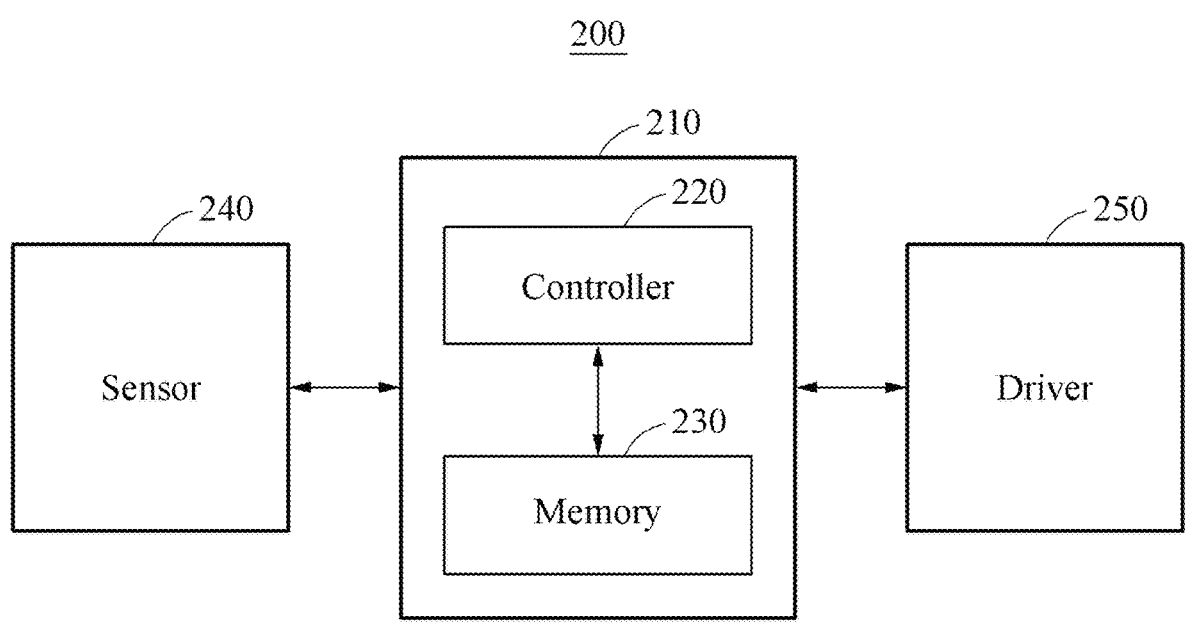
FIG. 2 is a diagram illustrating a configuration of a walking assist device according to at least one example embodiment.

FIG. 2 is a diagram illustrating a configuration of a walking assist device according to at least one example embodiment.

Referring to FIG. 2, a walking assist device 200 includes a sensor 240, a control device 210, and a driver 250. The control device 210 may be a device for controlling the walking assist device 200. According to an example, the walking assist device 200 may further include a support member to support a body of a user wearing the walking assist device 200 and a fixing member to be fastened to the body of the user. For example, the walking assist device 200 may be the walking assist device 110 of FIG. 1 such that the control device 210 corresponds to the controller 130 of FIG. 1.

The sensor 240 may include various sensors. The sensor 240 may include a sensor configured to sense information associated with a walking movement, or a gait, of the user, and a sensor configured to sense information needed to control an operation of the walking assist device 200. For example, the sensor 240 may include a sensor (e.g., acceleration sensor, inertial sensor, and gyro sensor) configured to measure a gait of the user, a torque sensor configured to measure an assist torque transferred by the driver 250, a current/voltage sensor, and the like.

In an example, the gait of the user may be measured through a sensor sensing angle information or motion information of both hip joints corresponding to positions of the hip joints of both legs of the user. The angle information of the hip joints may include at least one set of information associated with angles of the hip joints, a difference between the angles of the hip joints, motion directions of the hip joints, and angular velocities of the hip joints.

The control device 210 configured to control the walking assist device 200 includes a controller 220 and a memory 230. The memory 230 is connected to the controller 220, and configured to store instructions to be executed by the controller 220, and data to be processed by the controller 220 and/or data having been processed by the controller 220. For example, the memory 230 stores parameters corresponding to an assist torque control signal output by the controller 220. The memory 230 may include a non-transitory computer-readable storage medium, for example, a high-speed random-access memory (RAM) and/or a nonvolatile computer-readable storage medium (e.g., at least one disk storage device, flash memory device, or other nonvolatile solid-state memory devices).

The controller 220 may be implemented using processing circuitry such as hardware including logic circuits, a hardware/software combination such as a processor executing software; or a combination thereof. For example, the processing circuitry may include, but is not limited to, a central processing unit (CPU), an arithmetic logic unit (ALU), a digital signal processor, a microcomputer, a field programmable gate array (FPGA), a System-on-Chip (SoC) a programmable logic unit, a microprocessor, or an application-specific integrated circuit (ASIC), etc.

The controller 220 generates a control signal to control the walking assist device 200. For example, the controller 220 generates a torque control signal to control an assist torque to be provided by the walking assist device 200 based on the gait measured by the sensor 240. The controller 220 controls the driver 250 configured to generate the assist torque in the walking assist device 200 based on the generated control signal.

As discussed in more detail below, the controller 220 may be programmed as a special purpose processor to perform reinforcement learning such that the walking assist device 200 may improve assist torque transfer power by increasing a rate at which the assist torque provided to the user by the walking assist device 200 is useful for the user when walking, and reduce the number of mismatches in walking assistance by decreasing a rate at which the assist torque provided to the user by the walking assist device 200 hinders the user from walking.

The driver 250 operates an actuator of the walking assist device 200 based on the torque control signal generated by the controller 220. The driver 250 provides the assist torque to the gait of the hip joints of the user through the actuator. The actuator converts electrical energy to kinetic energy, and applies the kinetic energy to the body of the user to provide the user with power needed for the user to walk. The actuator is disposed on a portion corresponding to the positions of the hip joints of the user, and generates the assist torque for flexion and extension of the legs of the user to assist the user in walking.

The controller 220 determines a state variable indicating a gait state of the user based on the gait of the user, and controls the walking assist device 200 based on the determined state variable. The controller 220 sets a parameter to control the assist torque based on the state variable, and outputs a periodic assist torque control signal to assist the user in walking based on the set parameter.

In an example, the controller 220 controls an assist torque to be provided by the walking assist device 200 based on a state variable, and determines whether to individualize a control signal used to control the assist torque based on the state variable. The controller 220 sets a gain to adjust an intensity of the assist torque and sets a time delay to adjust an output time of the assist torque, and defines the state variable based on the set gain and the set time delay. By adjusting the gain and the time delay, the walking assist device 200 may more stably respond to a sudden motion of the user, a sudden stop of the user, or a change in environment, and to improve levels of walking regularity and safety. A first state variable, a second state variable, and a third state variable to be described hereinafter may be used to define the assist torque control signal that is used to control the operation of the walking assist device 200.

In an example, the controller 220 determines a first state variable for a gait state of the user based on a walking movement, or a gait, of the user. The controller 220 smooths the first state variable and time-delays the smoothed first state variable to obtain a second state variable which is smoothed and time-delayed from the first state variable. In this example, the term "time-delay" may indicate a process performed using a time delay which is a time value set (or, alternatively, preset) by the user or based on a control design rule. For example, when a walking speed of the user is greater than a first reference value, the controller 220 sets a time delay to be relatively small. Conversely, when a walking speed of the user is less than the first reference value, the controller 220 sets a time delay to be relatively large. For another example, the controller 220 determines a delay based on a walking acceleration of the user. In this example, when a walking acceleration of the user is greater than a second reference value, the controller 220 sets a time delay to be small. Conversely, when a walking acceleration of the user is less than the second reference value, the controller 220 sets a time delay to be large. In the foregoing examples, the walking speed and the walking acceleration of the user may be determined based on sensing information obtained from the sensor 240.

The controller 220 obtains a third state variable by applying a torque control variable to the second state variable. The controller 220 determines a gait phase in a gait cycle of the user based on the first state variable, and determines the torque control variable when the determined gait phase corresponds to a defined or (alternatively, a predefined) gait phase.

The torque control variable is determined in different ways in a learning mode and in a normal mode. The user may select the learning mode or the normal mode. The user may select the learning mode to optimize or individualize the walking assist device 200. Through the learning mode, parameters associated with controlling an assist torque to be provided by the walking assist device 200 may be adjusted based on a gait state or a gait style of the user.

When the normal mode is selected, the controller 220 determines a desired (or, alternatively, an optimal) torque control variable by applying a state variable value corresponding to a current gait phase of the user to a torque control variable determining function based on parameters derived from a previous learning result. The controller 220 determines the determined torque control variable to be the torque control variable to be applied to the second state variable.

When the learning mode is selected, the controller 220 determines, to be the torque control variable, a retrieval torque control variable generated based on a probability function. In an example, in the learning mode, the controller 220 determines a score of a previous torque control variable based on a walking assist power index determined from a previous gait of the user. The walking assist power index includes a first walking assist power index indicating a magnitude of walking assistance power transferred by the walking assist device 200, and a second walking assist power index indicating a degree of hindrance to the user in walking by the walking assist device 200. The first walking assist power index is a positive measurement result value for walking assistance, and the second walking assist power index is a negative measurement result value for walking assistance. For example, the controller 220 calculates the score in a form of weighted sum of the first walking assist power index and the second walking assist power index.

The walking assist power index may be calculated in real time, and a control policy of the walking assist device 200 may be learned based on the walking assist power index. In the learning mode, a parameter of the probability function may be determined such that the first walking assist power index increases and the second walking assist power index decreases, and the retrieval torque control variable may be determined based on the probability function. When the score determined based on the walking assist power index does not satisfy a set (or, alternatively, a preset) condition, the controller 220 generates the retrieval torque control variable based on the probability function, and determines the generated retrieval torque control variable to be the torque control variable to be applied to the second state variable. The set (or, alternatively, preset) condition may indicate that the score is greater than a threshold value, or the number of times calculating the score reaches a certain number of times.

The controller 220 obtains a third state variable by smoothing the determined torque control variable and applying the smoothed torque control variable to the second state variable. The controller 220 generates a control signal to determine the assist torque to be provided by the walking assist device 200 based on the obtained third state variable. The controller 220 generates an assist torque control signal by applying, to the third state variable, a gain for adjusting an intensity of the assist torque, and controls the assist torque to be provided by the walking assist device 200 based on the generated assist torque control signal.

Through the operations described above, it is possible to reduce the number of mismatches in walking assistance provided by the walking assist device 200, improve an assist torque transfer efficiency, and/or improve a level of walking regularity. For example, through reinforcement learning, the walking assist device 200 may improve assist torque transfer power by increasing a rate at which the assist torque provided to the user by the walking assist device 200 is useful for the user when walking, and reduce the number of mismatches in walking assistance by decreasing a rate at which the assist torque provided to the user by the walking assist device 200 hinders the user from walking.

According to an example, a remote controller (not shown) configured to remotely control the walking assist device 200 may be provided. The remote controller may control an overall operation of the walking assist device 200 in response to an input from the user. For example, the remote controller may initiate or suspend the operation of the walking assist device 200. In addition, the remote controller may generate an assist torque control signal to control a walking assistance operation of the walking assist device 200, and transmit the generated assist torque control signal to the walking assist device 200. The remote controller may provide a user interface (UI) that facilitates manipulation or operation of the walking assist device 200. Through the UI, the user may directly set a gain associated with an intensity of an assist torque to be provided by the walking assist device 200 or a delay in an output time of the assist torque.

Figure 3:
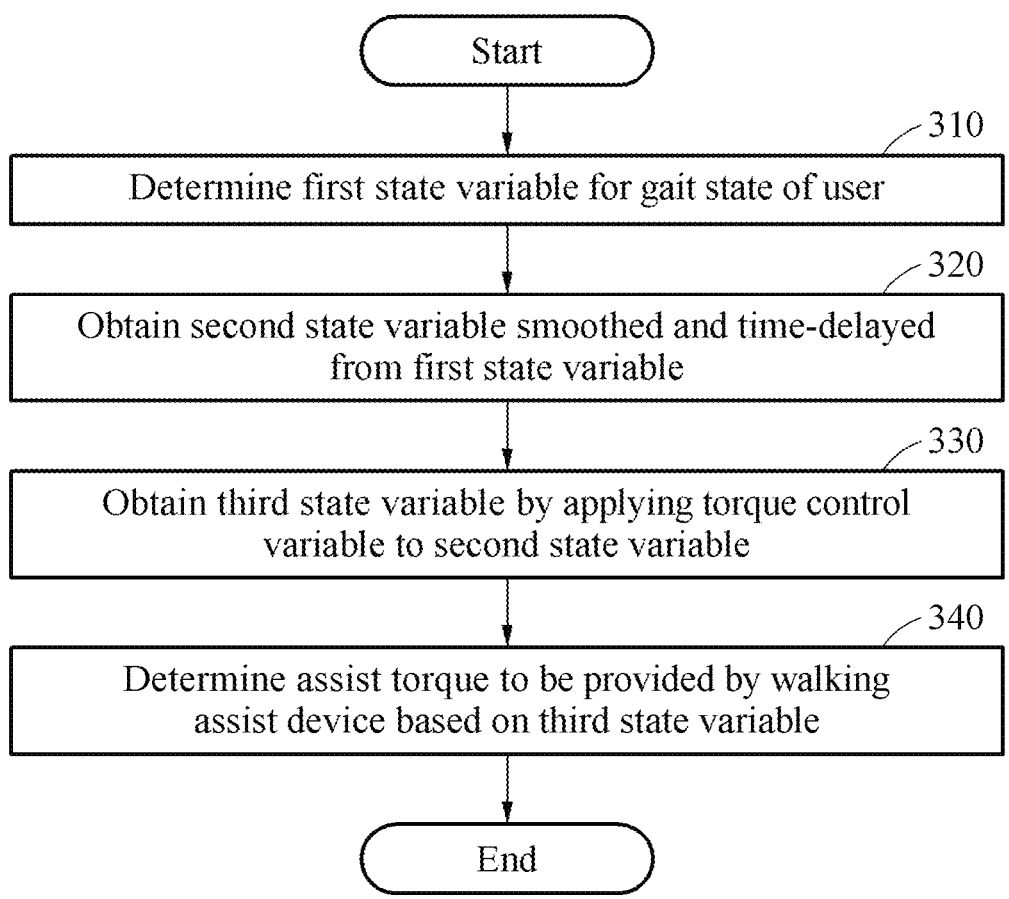
FIGS. 3 and 4 are flowcharts illustrating a method of controlling a walking assist device according to at least one example embodiment.
Figure 4:
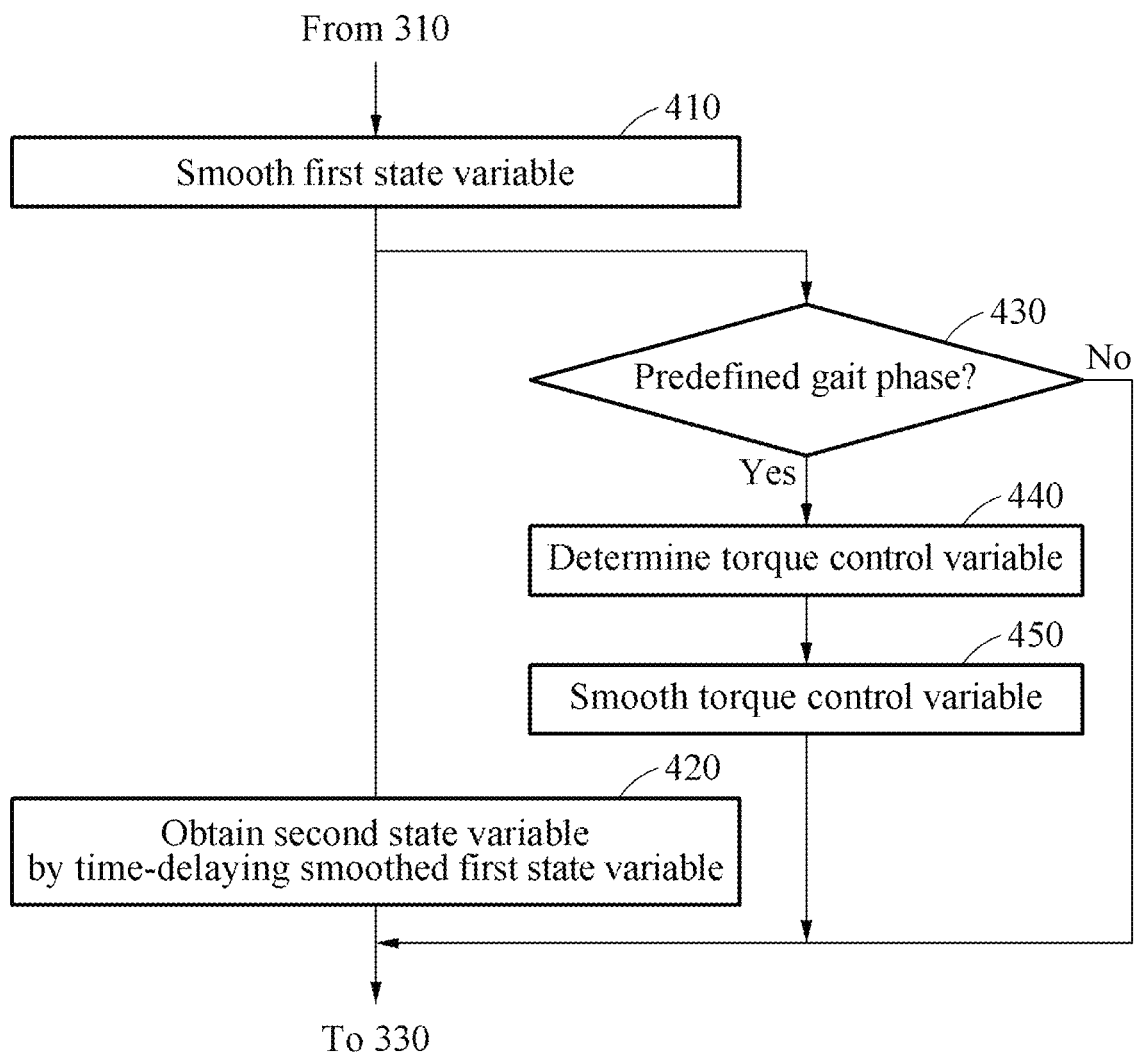

FIGS. 3 and 4 are flowcharts illustrating a method of controlling a walking assist device according to at least one example embodiment. The method of controlling a walking assist device will be hereinafter simply referred to as a control method, and the control method may be performed by a device for controlling a walking assist device which will be hereinafter simply referred to as a control device, which may be, for example, the control device 210.

Referring to FIG. 3, in operation 310, a control device determines a first state variable for a gait state of a user wearing a walking assist device based on a gait of the user. For example, the control device determines the first state variable based on hip joint angle information of the user that is measured by a sensor of the walking assist device. The first state variable may indicate a gait or a movement of the user in association with the gait state of the user, and may be defined by angle information of left and right hip joints as represented by Equation 1.

$$y_2(t) = \sin q_r(t) - \sin q_l(t) \qquad \text{[Equation 1]}$$

In Equation 1, $y_2(t)$ denotes a first state variable based on time t. $q_r(t)$ and $q_l(t)$ denote an angle of a right hip joint and an angle of a left hip joint, respectively, based on time t.

In operation 320, the control device obtains a second state variable which is smoothed and time-delayed from the first state variable. Operation 320 may be performed in detail as described hereinafter with reference to FIG. 4. Referring to FIG. 4, in operation 410, the control device smooths the first state variable. Through the smoothing, noise in the first state variable may be reduced. The control device may smooth the first state variable using a smoothing filter including, for example, a low-pass filter (LPF). The control device may obtain the smoothed first state variable by performing low-pass filtering based on a first state variable determined for a current gait cycle and a first state variable determined for a previous gait cycle, as represented by Equation 2.

$$y = (1-\alpha)y_{prev} + \alpha y_{raw}, (0 \leq \alpha \leq 1) \qquad \text{[Equation 2]}$$

In Equation 2, y denotes a smoothed first state variable, and $\alpha$ denotes a defined (or, alternatively, a predefined) constant having a value between 0 and 1. $y_{prev}$ denotes a first state variable determined for a previous gait cycle, and $y_{raw}$ denotes a first state variable determined for a current gait cycle.

In operation 420, the control device obtains the second state variable by time-delaying the smoothed first state variable obtained in operation 410. In another example, the time-delaying may be performed prior to the smoothing. In this example, the second state variable may be obtained by performing the smoothing, such as, for example, filtering, on the time-delayed first state variable obtained through the time-delaying. In the time-delaying process, a time delay value applied to the first state variable may be a defined (or, alternatively, a predefined) value or a value set by the user.

In operation 430, the control device determines whether a gait phase of the user corresponds to a defined (or, alternatively, a predefined) gait phase. The control device calculates a current gait phase based on the smoothed first state variable obtained in operation 410 as represented by Equation 3.

$$\phi = \frac{1}{2\pi}(\text{atan2}(cy, \dot{y}) - \pi), c = 6 \quad \text{[Equation 3]}$$

In Equation 3, φ denotes a gait phase, and y denotes a smoothed first state variable. The calculated gait phase may be periodic based on a gait of the user.

In operation 440, when the gait phase of the user corresponds to the defined (or, alternatively, a predefined) gait phase, the control device determines a torque control variable. The torque control variable may be used to more finely adjust a point in time at which an assist torque control signal is to be applied. In a mode which is not a learning mode, a previously determined torque control variable or a defined (or, alternatively, a predefined) torque control variable may be used. However, in the learning mode, a desired (or, alternatively, an optimal) torque control variable may be retrieved based on a gait of the user. The learning mode may be a process for individualizing the walking assist device to be suitable for the user, and whether to enter the learning mode or not may be selected by the user. Hereinafter, how to determine a torque control variable will be described in detail with reference to FIG. 5.

In operation 450, the control device smooths the torque control variable determined in operation 440. In an example, the torque control variable determined in operation 440 may change discontinuously and such a discontinuous change of the torque control variable may generate a relatively great jerk motion, which may pose a threat to the safety of the user and the walking assist device. Thus, a consistent reaction may not be readily derived from the user. To inhibit (or, alternatively, prevent) this, the control device may smooth the torque control variable such that the torque control variable is gradually applied. By the smoothed torque control variable, an assist torque to be provided to the walking assist device may continuously and smoothly change. Thus, the jerk motion may not be generated in the walking assist device, and safe and stable interactive learning may occur between the user and the walking assist device.

When the gait phase of the user does not correspond to the defined (or, alternatively, a predefined) gait phase as a result of the determination in operation 430, the torque control variable applied to a previous cycle may be applied unchanged to a current cycle.

Referring back to FIG. 3, in operation 330, the control device obtains a third state variable by applying the torque control variable to the second state variable. In operation 340, the control device determines an assist torque to be provided by the walking assist device based on the obtained third state variable. The control device generates an assist torque control signal by applying, to the third state variable, a gain for adjusting an intensity of the assist torque, and controls the assist torque to be provided by the walking assist device based on the generated assist torque control signal. The assist torque controlled in such a manner is applied during one gait cycle of the user. When the gait cycle is terminated, operations 310 through 340 are performed again on a next gait cycle.

According to at least one example embodiment, it is possible to effectively individualize a walking assist device to be suitable to a user of the walking assist device based on a gait characteristic of the user, and to improve safety of both the user and the walking assist device by smoothly controlling an assist torque to be provided by the walking assist device.

Figure 5:
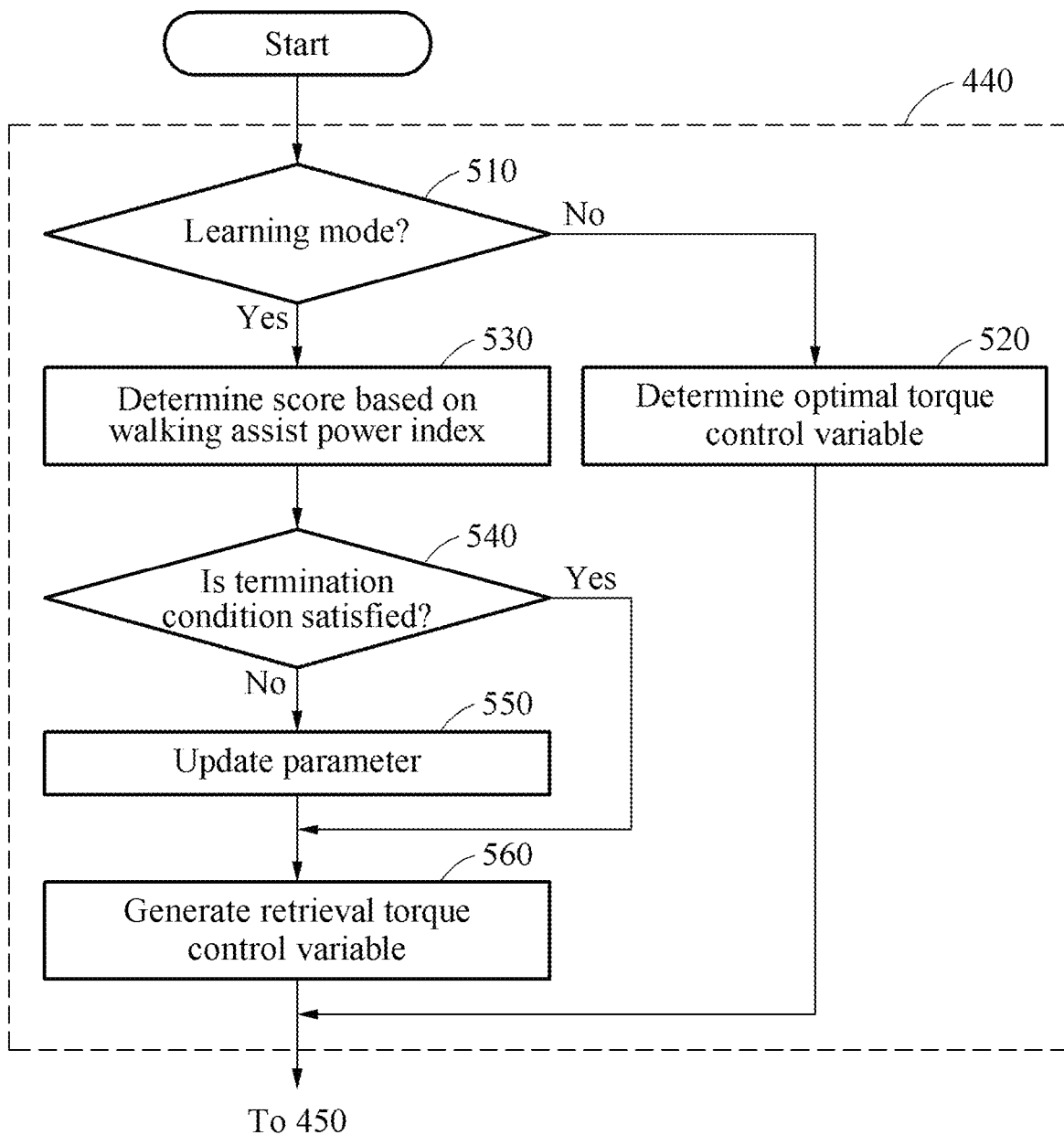
FIG. 5 is a flowchart illustrating a method of determining a torque control variable according to at least one example embodiment.

FIG. 5 is a flowchart illustrating a method of determining a torque control variable according to at least one example embodiment.

Referring to FIG. 5, when determining the torque control variable in operation 440, the controller may perform operations 510 to 560, discussed below.

In operation 510, a control device determines whether a current set mode is a learning mode. In an example, a user may adjust a mode of a walking assist device to be the learning mode or a normal mode.

In operation 520, when the current set mode is the normal mode, the control device determines a desired (or, alternatively, an optimal) torque control variable without a learning process. For example, the control device determines the desired (or, alternatively, optimal) torque control variable by applying a state variable value corresponding to a current gait phase of the user to a torque control variable determining function based on parameters derived from a previous learning result. In an example, when learning is already completed and the normal mode operates currently, the control device sets a control policy suitable to a current gait state of the user using parameters obtained from a previous learning process, and determines the desired (or, alternatively, optimal) torque control variable using the set control policy. In another example, the control device uses a previously determined optimal torque control variable. The control device determines the determined torque control variable to be a torque control variable to be applied to a second state variable.

When the current set mode is the learning mode, the control device performs reinforcement learning including operations 530 through 560. Such a learning process may be performed once per gait cycle of the user.

In operation 530, the control device determines a score, for example, a reward, for a previous torque control variable based on a walking assist power index determined for a previous gait of the user. The walking assist power index includes a first walking assist power index indicating a magnitude of walking assistance power transferred from the walking assist device, and a second walking assist power index indicating a degree of hindrance to the user in walking by the walking assist device. In an example, the first walking assist power index indicates how assist power is well transferred to the user for walking. The greater the first walking assist power index the greater the assist power to be transferred. In addition, the second walking assist power index indicates a quantity of hindrance to the user in walking and is indicated by a negative value. The smaller the value the greater the resistance of the hindrance to the user in walking.

In an example, the score may be determined based on a weighted sum of the first walking assist power index and the second walking assist power index as represented by Equation 4.

$$\text{Score (reward)} = 0.25\text{MPP} + 5\text{MNP} \quad \text{[Equation 4]}$$

In Equation 4, MPP (Mean Positive Power) and MNP (Mean Negative Power) denote a first walking assist power index and a second walking assist power index, respectively. In Equation 4, weights applied to MPP and MNP are provided as examples, and the weights may vary according to an example. For example, when one cycle of learning is applied per gait cycle, MPP and MNP indicate a mean value of the first walking assist power index and a mean value of the second walking assist power index, respectively, for a gait during a previous gait cycle, for example, two steps or one stride. Equation 4 above may be an objective function for adjusting a learning result to be desirable.

When the score represented by the weighted sum of the first walking assist power index and the second walking assist power index increases, the walking assistance to be provided may be smoother, without hindrance to the user in walking while naturally great assist power is being provided. The learning process may be performed in accordance with a current gait state of the user. For example, the learning process may be performed such that a value of the first walking assist power index increases while an absolute value of the second walking assist power index does not excessively increase.

In operation 540, the control device determines whether a termination condition is satisfied. The termination condition indicates whether the score determined in operation 530 exceeds a threshold value, or whether the number of repetitions of the learning process reaches a defined (or, alternatively, a predefined) number of times. In operation 550, when the termination condition is not satisfied, the control device updates a parameter of a probability model for determining a retrieval torque control variable. The control device updates the parameter of the probability model such that the score increases. The updating of the parameter may be performed repetitively on each gait cycle until the termination condition is satisfied.

In operation 560, the control device generates the retrieval torque control variable based on a probability model-based function. The control device generates the retrieval torque control variable based on the probability model-based function, and determines the generated retrieval torque control variable to be the torque control variable to be applied to the second state variable.

A score for a retrieval torque control variable newly determined in each learning process may be measured, and a parameter of the probability model may be updated repetitively until the termination condition is satisfied.

Figure 6:
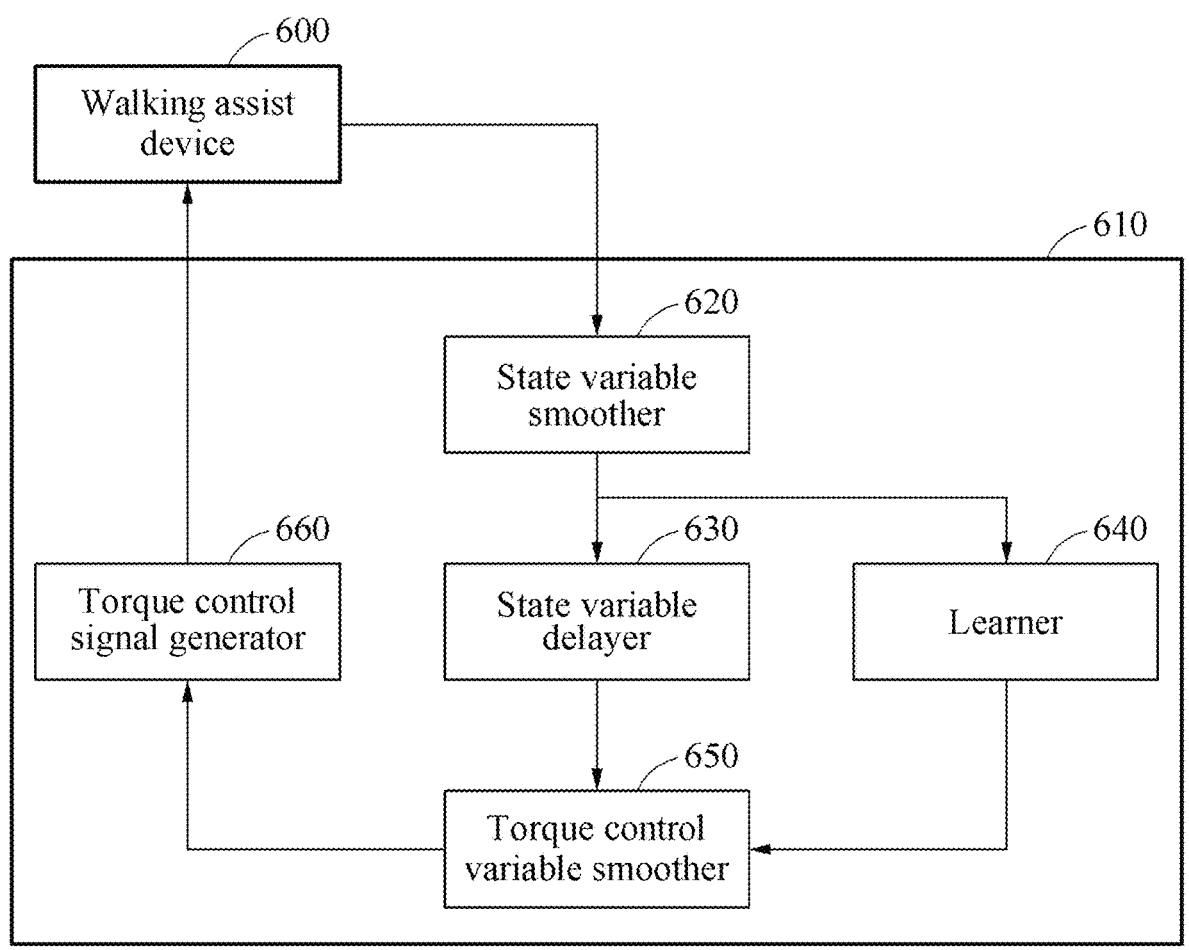
FIG. 6 is a diagram illustrating a configuration of a device for controlling a walking assist device according to at least one example embodiment.

FIG. 6 is a diagram illustrating a configuration of a control device for controlling a walking assist device according to at least one example embodiment.

Referring to FIG. 6, a control device 610 of a walking assist device 600 may correspond to the control device 210 of FIG. 2.

The control device 610 may include a state variable smoother 620, a state variable delayer 630, a learner 640, a torque control variable smoother 650, and a torque control signal generator 660.

For example, as discussed in more detail below, the processing circuitry included in the control device 610 may be configured as a special purpose processor to perform the operations of the state variable smoother 620, the state variable delayer 630, the learner 640, the torque control variable smoother 650, and the torque control signal generator 660.

The control device 610 may use such components to safely and effectively individualize walking assistance to be suitable to a user of the walking assist device 600, and train or learn a control policy to be applied to the walking assist device 600. In an example, operations of the state variable smoother 620, the state variable delayer 630, the learner 640, the torque control variable smoother 650, and the torque control signal generator 660 may be performed by the controller 220 described above with reference to FIG. 2.

Figure 7:
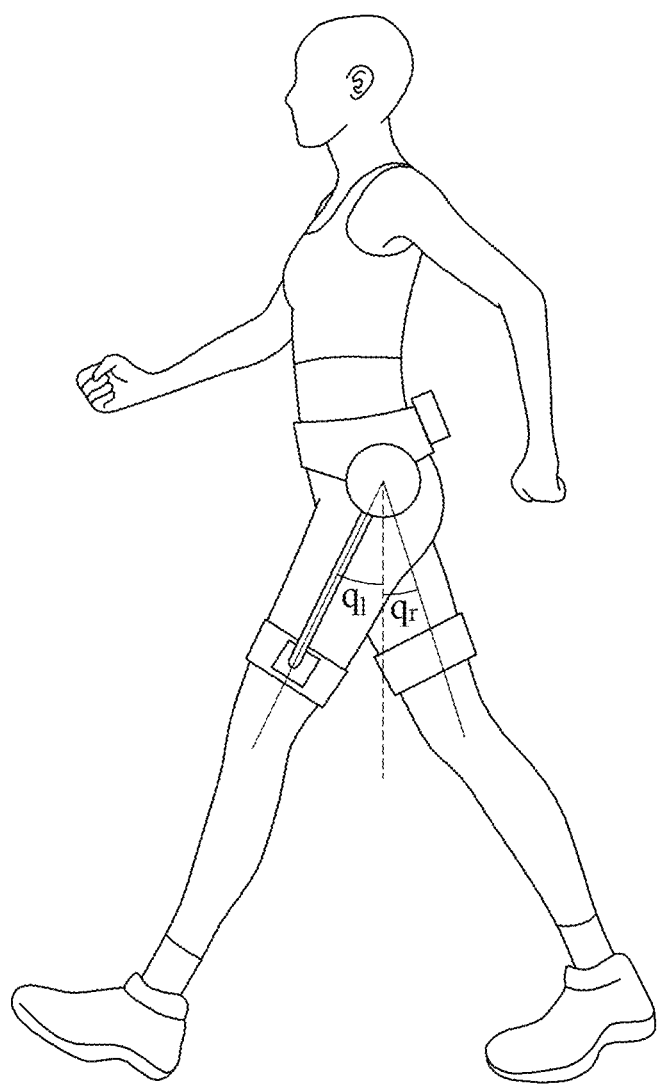
FIG. 7 is a diagram illustrating a method of determining a first state variable according to at least one example embodiment.

A first state variable for a gait state of the user is defined based on information associated with a gait of the user measured by a sensor of the walking assist device 600. Referring to FIG. 7, the sensor of the walking assist device 600 senses a left hip joint angle $q_l$ and a right hip joint angle $q_r$ associated with a current gait of the user. To the control device 610, left hip joint angle information and right hip joint angle information sensed by the sensor are transferred. The control device 610 then determines the first state variable based on the left hip joint angle information and the right hip joint angle information. For example, the control device 610 calculates the first state variable based on the left hip joint angle information and the right hip joint angle information as represented by Equation 1 above.

Figure 8:
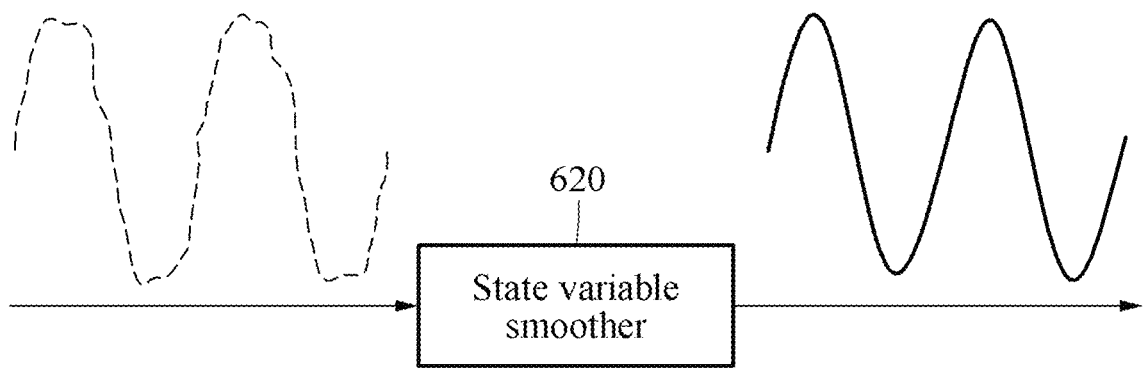
FIG. 8 is a diagram illustrating an operation of a state variable smoother according to at least one example embodiment.

Referring back to FIG. 6, the state variable smoother 620 smooths the first state variable determined based on the sensed hip joint angle information to change the first state variable to a smoother signal. Such a smoothing process may include, for example, low-pass filtering as represented by Equation 2 above. Referring to FIG. 8, a first state variable which includes noise or is not smooth is input to the state variable smoother 620, and the state variable smoother 620 changes the input first state variable to a smoother signal and outputs the smoother signal using a filter.

Figure 9:
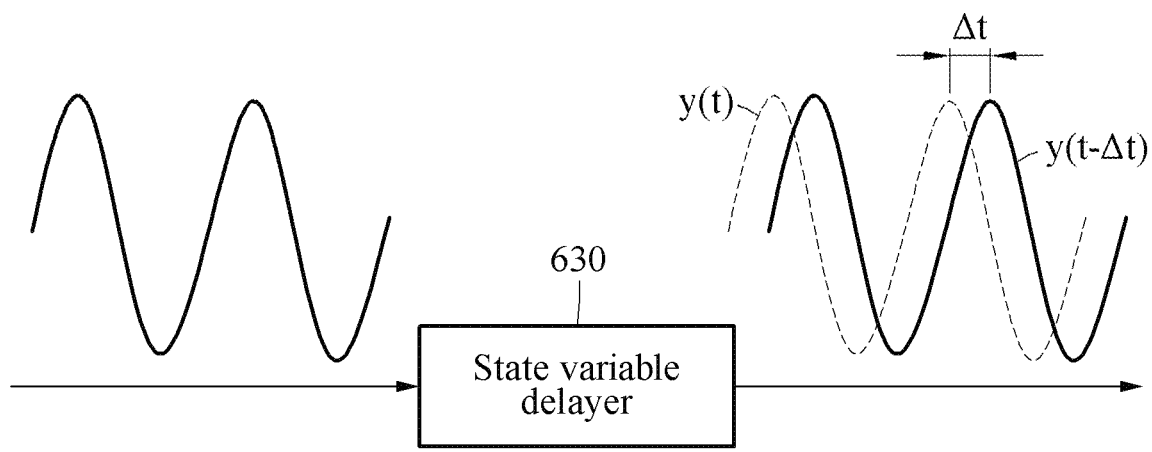
FIG. 9 is a diagram illustrating an operation of a state variable delayer according to at least one example embodiment.

Referring back to FIG. 6, the state variable delayer 630 time-delays the smoothed first state variable, and outputs a second state variable as a result of performing the time-delaying. The second state variable corresponds to a result of smoothing the first state variable calculated as represented by Equation 1 above and then time-delaying the smoothed first state variable. Referring to FIG. 9, a smoothed first state variable y(t) is input to the state variable delayer 630, and the state variable delayer 630 applies a time delay Δt to the input first state variable y(t) and outputs a second state variable y(t−Δt). The time delay Δt determines an output time of a increased (or, alternatively, a maximum) assist torque and may be a value set by the user, for example, a constant.

Referring back to FIG. 6, the learner 640 estimates a current gait phase of the user based on the smoothed first state variable. For example, the learner 640 estimates a gait phase based on Equation 5.

$$\text{phase} = \frac{1}{2\pi} \text{atan2}(cy(t-\Delta t), \dot{y}(t-\Delta t)) \quad \text{[Equation 5]}$$

In Equation 5, phase denotes a gait phase of a user, and y(t) denotes a smoothed first state variable. Δt denotes a time delay, and c denotes a defined (or, alternatively, a predefined) constant as a scaling factor for scaling. An example of a change of the gait phase calculated based on Equation 5 above over time will be described hereinafter with reference to FIG. 10.

Figure 10:
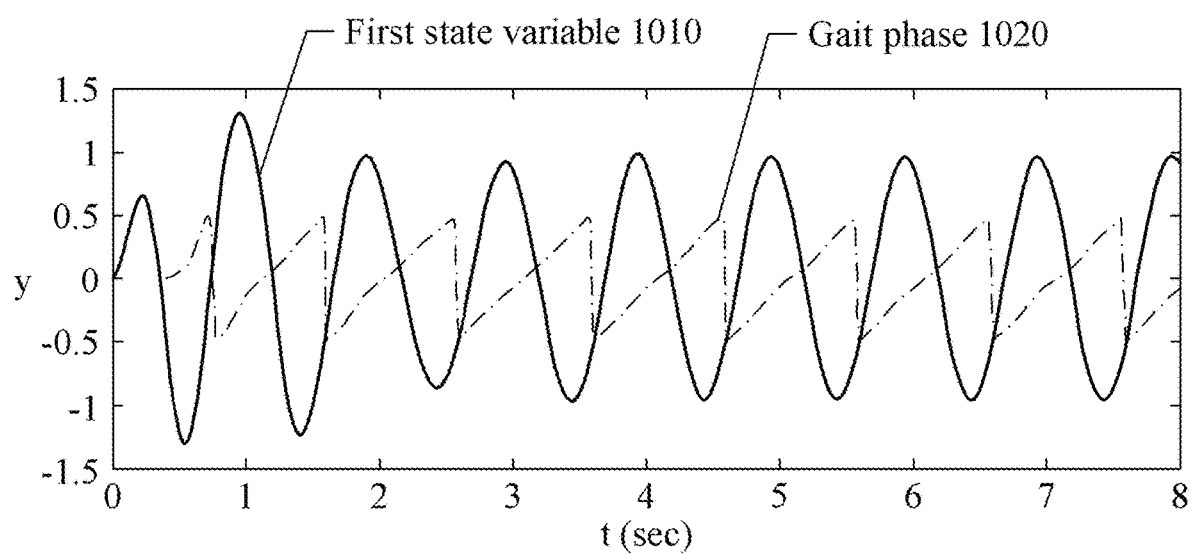
FIG. 10 is a graph illustrating a relationship between a first state variable and a gait phase according to at least one example embodiment.

FIG. 10 illustrates a graph indicating a change of a smoothed first state variable 1010 over time and a change of a gait phase 1020 determined based on the first state variable 1010 over time. Both the first state variable 1010 and the gait phase 1020 have periodicity.

Referring back to FIG. 6, the learner 640 determines whether a current gait phase corresponds to a defined (or, alternatively, a predefined) gait phase. When the current gait phase corresponds to the defined (or, alternatively, a predefined) gait phase, the learner 640 determines a torque control variable. When a set mode is a learning mode, the learner 640 retrieves a torque control variable to improve (or, alternatively, optimize) a point in time at which an assist torque control signal is to be applied by performing reinforcement learning. When the reinforcement learning is performed, the learner 640 calculates a score based on a first walking assist power index and a second walking assist power index. The learner 640 determines parameters of a probability model-based function based on the calculated score and the first state variable, and generates a retrieval torque control variable based on the probability model-based function. The retrieval torque control variable may be used to finely adjust a time delay applied by the state variable delayer 630. Herein, a learning process may be a process of finely adjusting the time delay based on the retrieval torque control variable, and discovering the retrieval torque control variable such that the score calculated as a result of the adjusting is increased (or, alternatively, maximized). Such learning process may be performed on a certain gait phase.

In a normal mode which is not the learning mode, the learner 640 determines a desired (or, alternatively, an optimal) torque control variable without performing the learning process. For example, the learner 640 determines the desired (or, alternatively, optimal) torque control variable by applying a state variable value corresponding to a current gait phase of the user to a torque control variable determining function based on parameters derived from a previous learning result. The desired (or, alternatively, optimal) torque control variable may also be used to finely adjust a time delay applied by the state variable delayer 630.

Figure 11:
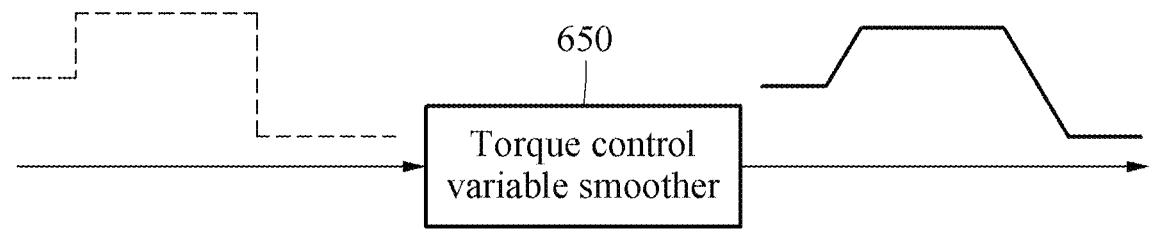
FIG. 11 is a diagram illustrating an operation of a torque control variable smoother according to at least one example embodiment.
Figure 13A:
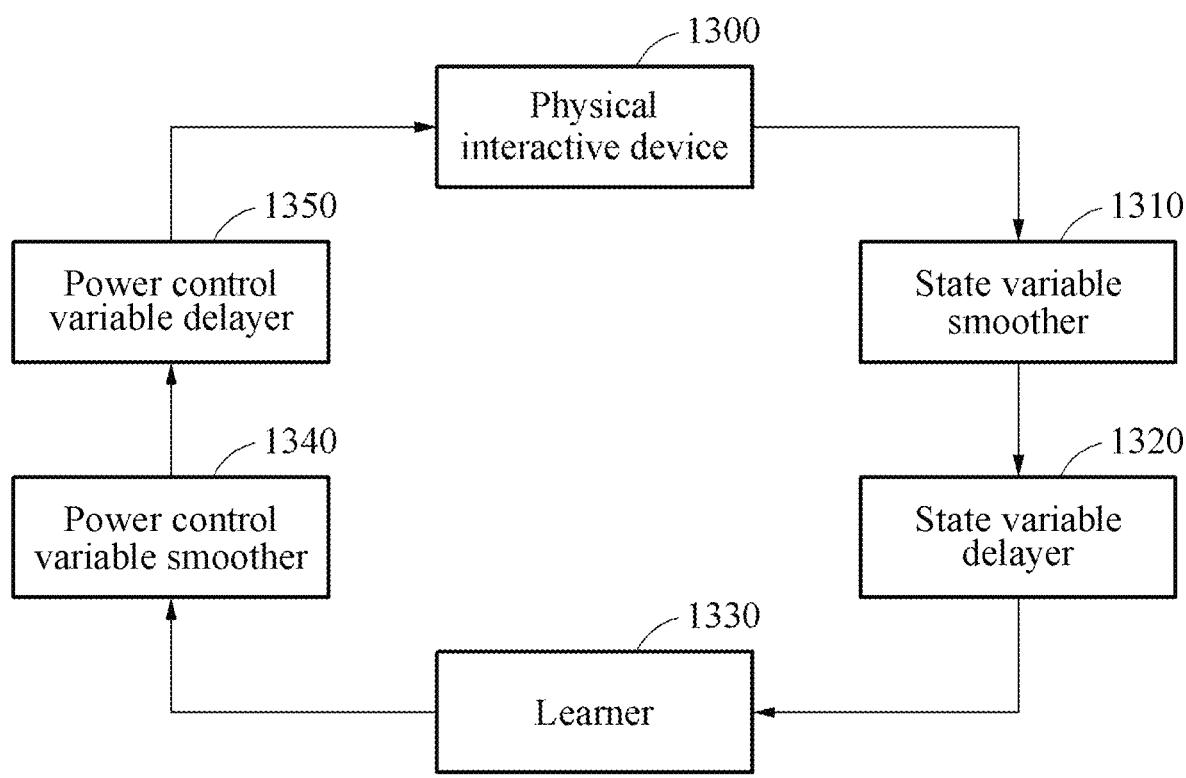
FIGS. 13A through 13D are diagrams illustrating different examples of a system for controlling a physical interactive device according to at least one example embodiment.
Figure 13B:
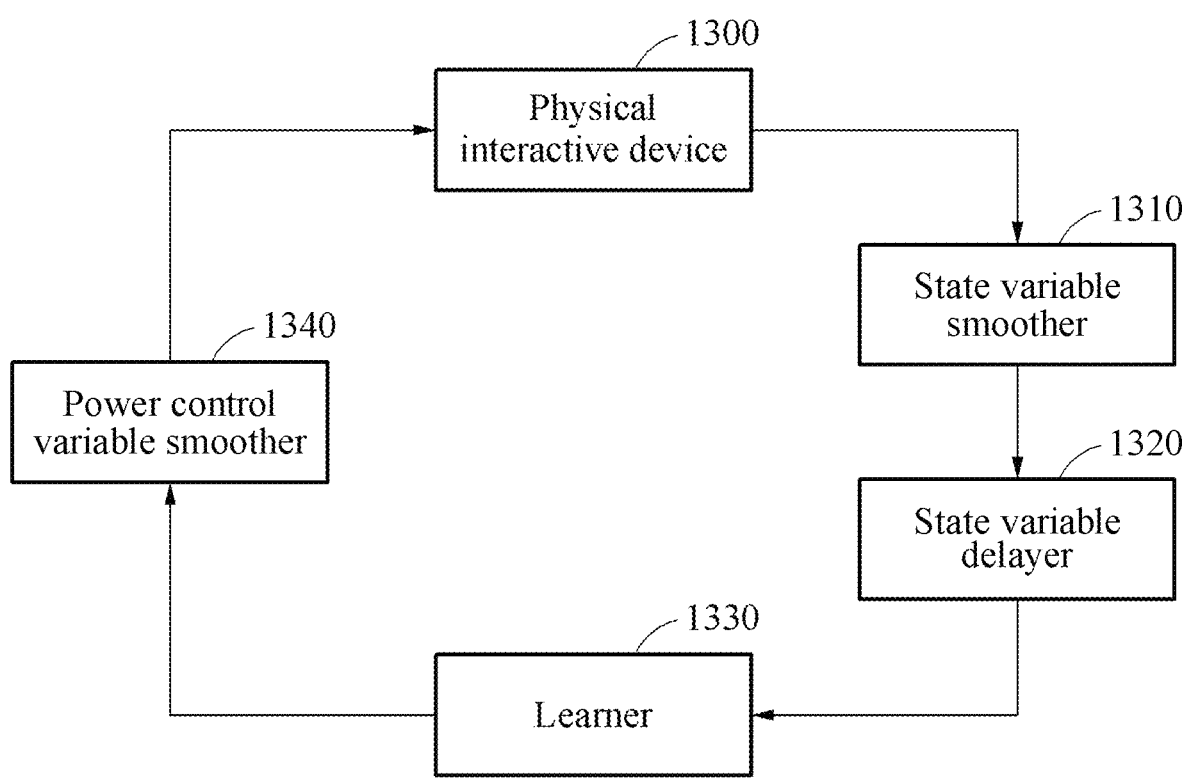
Figure 13C:
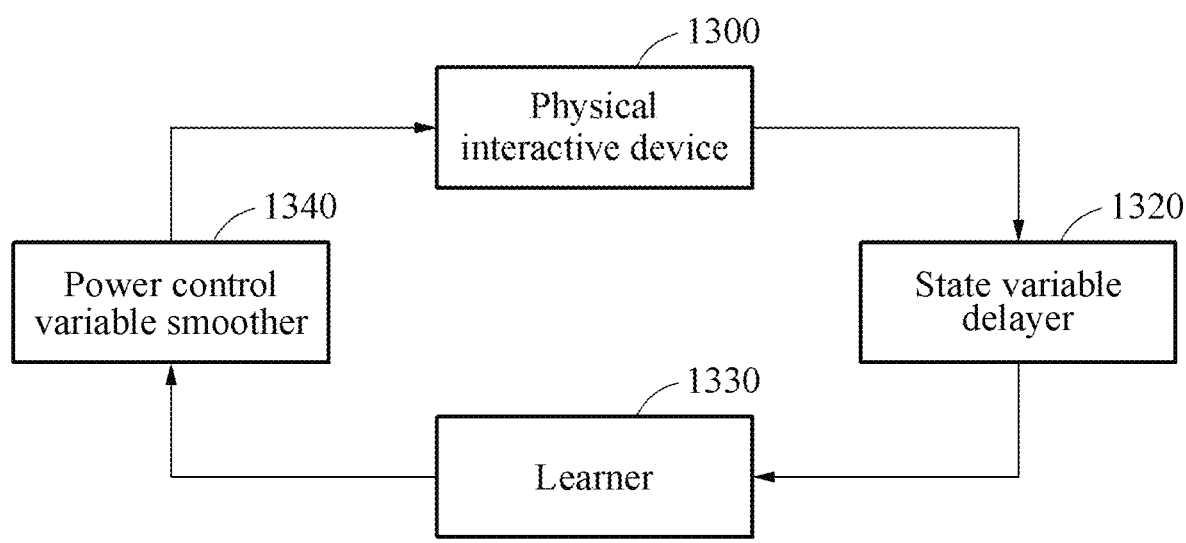
Figure 13D:
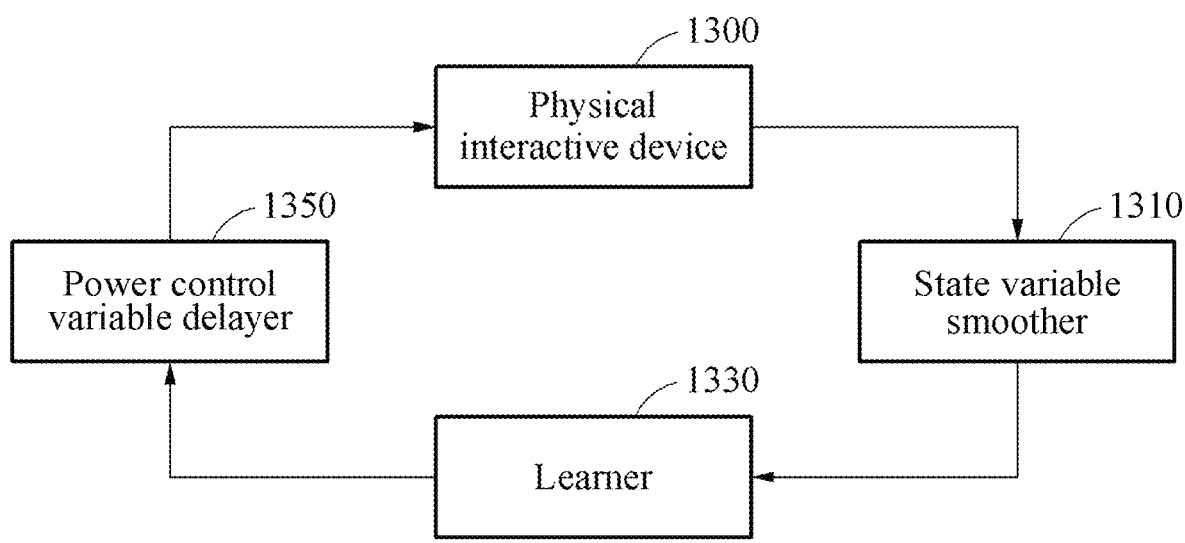

The torque control variable smoother 650 smooths the retrieval torque control variable or the optimal torque control variable. Referring to FIG. 11, the torque control variable smoother 650 performs such smoothing process such that a torque control variable changes gradually around a time point to which the torque control variable is applied and around a time point in which the application is terminated. Thus, it is possible to inhibit (or, alternatively prevent) an assist torque provided by the walking assist device 600 from rapidly changing.

Referring back to FIG. 6, the torque control variable smoother 650 generates a third state variable by applying the smoothed torque control variable to the second state variable output from the state variable delayer 630, and outputs the generated third state variable. The torque control signal generator 660 generates an assist torque control signal based on the third state variable, and transmits the generated assist torque control signal to the walking assist device 600. The torque control signal generator 660 generates the assist torque control signal by applying, to the third state variable, a gain for adjusting an intensity of the assist torque. The assist torque control signal may be maintained for one gait cycle of the user. In an example, the torque control signal generator 660 inverts the assist torque control signal to generate the inverted assist torque control signal. The assist torque control signal may be applied to assist a left leg of the user with walking, and the inverted assist torque control signal may be applied to assist a right leg of the user with walking.

FIG. 12 is a diagram illustrating a configuration of a system for controlling a physical interactive device according to at least one example embodiment. The system for controlling a physical interactive device will be hereinafter simply referred to as a control system.

Referring to FIG. 12, the example embodiments described above with reference to FIGS. 1 through 11 are expandable and applicable to control a physical interactive device 1200 which is physically interactive with humans. The physical interactive device 1200 includes, for example, a wheel-based mobile robot, an articulated robotic limb, a biped walking humanoid robot, and the like.

When there is a physical interaction between a user and the physical interactive device 1200, a control device 1210 configured to control the physical interactive device 1200 may smooth or intentionally time-delay a control signal used to control the physical interactive device 1200 for the safety of the user and the physical interactive device 1200. Similar to the control device 610 of the walking assist device 600 illustrated in FIG. 6, the control device 1210 includes a state variable smoother 1220, a state variable delayer 1230, a learner 1240, a power control variable smoother 1250, and a power control signal generator 1260. Respective operations of such components of the control device 1210 respectively correspond to the operations of the components of the control device 610, and thus detailed descriptions of the operations will be omitted here for brevity. However, the control device 1210 of FIG. 12 may differ from the control device 610 of FIG. 6 in that the control device 1210 generates a power control signal to control a driver of the physical interactive device 1200 through the power control signal generator 1260, whereas the control device 610 generates an assist torque control signal to control an assist torque of the walking assist device 600.

The learner 1240 determines whether a defined (or, alternatively, a predefined) event occurs based on information measured by a sensor of the physical interactive device 1200, and performs a learning process in response to the event occurring. For example, when there is a user-robot mutual contact or interaction, the learner 1240 learns a user-customized control operation of learning a reaction that is most preferred by the user, for example. A method of calculating a state variable, a score, and the like to be used for the learning may vary as described in the example of a walking assist device. In addition, the learner 1240 may perform the learning process using other optimization or learning algorithms, such as, for example, evolutionary computation, in addition to reinforcement learning.

As described above, the control device 1210 may facilitate a smoother and safer action-reaction interaction between the user and the physical interactive device 1200.

FIGS. 13A through 13D are diagrams illustrating different examples of a control system for controlling a physical interactive device according to at least one example embodiment.

Referring to FIGS. 13A through 13D, a control system for controlling a physical interactive device 1300 may be embodied by selective combinations of the physical interactive device 1300, a state variable smoother 1310, a state variable delayer 1320, a learner 1330, a power control variable smoother 1340, and a power control variable delayer 1350. In addition, a connection of components or elements in each selective combination may be embodied in various ways.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of controlling a walking assist device, the walking assist device configured to be worn by a user, the method comprising:

determining a first state variable for a gait phase of the user based on a gait of the user;
obtaining a second state variable by smoothing and time-delaying the first state variable;
determining a torque control variable based on the gait phase in a gait cycle of the user;
obtaining a third state variable by applying the torque control variable to the second state variable; and
determining an assist torque provided by the walking assist device based on the third state variable,
wherein, in a learning mode for individualizing the walking assist device to be suitable for the user, the determining of the torque control variable comprises updating a parameter associated with controlling the assist torque to be provided by the walking assist device by selectively adjusting the torque control variable during a set gait phase of each gait cycle by (i) determining a walking assistance power index indicating an efficiency of the assist torque provided by the walking assist device to the user during a previous gait cycle and, (ii) adjusting the torque control variable associated with a current gait cycle based on the walking assistance power index, and
wherein, in a normal mode, the determining of the torque control variable comprises determining the torque control variable based on the updated parameter derived from a learning result of the learning mode of the walking assist device.

2. The method of claim 1, further comprising:
smoothing the torque control variable to generate a smoothed torque control variable, wherein
the obtaining of the third state variable includes obtaining the third state variable by applying the smoothed torque control variable to the second state variable.

3. The method of claim 1, wherein, in the normal mode, the determining of the torque control variable comprises:
determining a desired torque control variable by applying a state variable value corresponding to a current gait phase in the gait cycle of the user to a torque control variable determining function based on the parameter derived from the previous learning result.

4. The method of claim 1, wherein, in the learning mode, the determining of the torque control variable comprises:
determining a retrieval torque control variable generated based on a probability function, and
setting the retrieval torque control variable as the torque control variable.

5. The method of claim 4, wherein, in the learning mode, the determining of the torque control variable further comprises:
determining a score of a previous torque control variable based on the walking assist power index determined from a previous gait of the user; and
determining whether the score satisfies a condition.

6. The method of claim 5, wherein
the walking assist power index includes,
a first walking assist power index indicating a magnitude of walking assist power transferred by the walking assist device, and
a second walking assist power index indicating a degree of hindrance to the user in walking by the walking assist device; and
the torque control variable is selectively adjusted based on the score by increasing the first walking assist power index in view of maintaining an absolute value of the second walking assist power index below a threshold.

7. The method of claim 6, wherein the determining of the score comprises:
   determining the score based on a weighted sum of the first walking assist power index and the second walking assist power index.

8. The method of claim 1, wherein the determining of the first state variable comprises:
   determining the first state variable based on hip joint angle information of the user measured by a sensor of the walking assist device.

9. The method of claim 1, wherein the first state variable is a discontinuous first state variable due to noise present therein, and the obtaining of the second state variable comprises:
   smoothing the first state variable by removing the noise from the discontinuous first state variable to generate a continuous first state variable; and
   obtaining the second state variable by time-delaying the continuous first state variable by a time delay that varies directly with a speed or acceleration of the user.

10. The method of claim 9, wherein the smoothing comprises:
    generating the continuous first state variable based on the first state variable determined for a current gait and the first state variable determined for a previous gait.

11. A non-transitory computer-readable medium comprising computer readable instructions that, when executed by a computer, cause the computer to perform the method of claim 1.

12. A device configured to control a walking assist device, the device comprising:
    a memory; and
    a controller configured to control an assist torque provided by the walking assist device based on a gait of a user wearing the walking assist device by,
       determining a first state variable for a gait phase of the user based on the gait,
       obtaining a second state variable by smoothing and time-delaying the first state variable,
       determining a torque control variable based on the gait phase in a gait cycle of the user,
       obtaining a third state variable by applying the torque control variable to the second state variable, and
       determining the assist torque to be provided by the walking assist device based on the third state variable,
          wherein, in a learning mode for individualizing the walking assist device to be suitable for the user, the determining of the torque control variable comprises updating a parameter associated with controlling the assist torque to be provided by the walking assist device by selectively adjusting the torque control variable during a set gait phase of each gait cycle by (i) determining a walking assistance power index indicating an efficiency of the assist torque provided by the walking assist device to the user during a previous gait cycle, and (ii) adjusting the torque control variable associated with a current gait cycle based on the walking assistance power index, and
          wherein, in a normal mode, the determining of the torque control variable comprises determining the torque control variable based on the updated parameter derived from a learning result of the learning mode of the walking assist device.

13. The device of claim 12, wherein the controller is configured to,
    determine the gait phase in the gait cycle of the user based on the first state variable.

14. The device of claim 13, wherein the controller is configured to, obtain the third state variable by,
    smoothing the torque control variable to generate a smoothed torque control variable, and
    applying the smoothed torque control variable to the second state variable.

15. The device of claim 13, wherein the controller is configured to operate in the learning mode to,
    determine the torque control variable,
    determine a score of a previous torque control variable based on the walking assist power index determined from a previous gait of the user,
    determine a retrieval torque control variable generated based on a probability function, in response to the score not satisfying a set condition, and
    set the retrieval torque control variable as the torque control variable.

16. The device of claim 15, wherein
    the walking assist power index includes,
       a first walking assist power index indicating a magnitude of walking assist power to be transferred by the walking assist device, and
       a second walking assist power index indicating a degree of hindrance to the user in walking by the walking assist device; and
    the controller is configured to adjust the torque control variable based on the score by increasing the first walking assist power index in view of maintaining an absolute value of the second walking assist power index below a threshold.

17. A walking assist device comprising:
    a sensor configured to measure a gait of a user wearing the walking assist device;
    a driver configured to operate an actuator of the walking assist device to provide an assist torque to the user based on a torque control signal; and
    a controller configured to generate the torque control signal to control the assist torque based on the gait measured by the sensor by,
       determining a first state variable for a gait phase of the user based on the gait,
       obtaining a second state variable by smoothing and time-delaying the first state variable,
       determining a torque control variable based on the gait phase in a gait cycle of the user,
       obtaining a third state variable by applying the torque control variable to the second state variable, and
       determining the assist torque provided by the walking assist device based on the third state variable,
    wherein, in a learning mode for individualizing the walking assist device to be suitable for the user, the determining of the torque control variable comprises updating a parameter associated with controlling the assist torque to be provided by the walking assist device by selectively adjusting the torque control variable during a set gait phase of each gait cycle by (i) determining a walking assistance power index indicating an efficiency of the assist torque provided by the walking assist device to the user during a previous gait cycle, and (ii) adjusting the torque control variable associated with a current gait cycle based on the walking assistance power index, and wherein, in a normal mode, the determining of the torque control variable comprises determining the torque control variable based on the updated parameter derived from a learning result of the learning mode of the walking assist device.

18. The walking assist device of claim 17, wherein the controller is configured to determine the gait phase in the gait cycle of the user based on the first state variable.

19. The walking assist device of claim 18, wherein the controller is configured to, obtain the third state variable by,
   smoothing the torque control variable to generate a smoothed torque control variable, and
   applying the smoothed torque control variable to the second state variable.

* * * * *